(12) United States Patent
Meek et al.

(10) Patent No.: US 10,449,417 B2
(45) Date of Patent: Oct. 22, 2019

(54) SYSTEM FOR OPTIMAL PHYSICAL EXERCISE AND TRAINING

(71) Applicant: Intelidigital Corp., Valencia, CA (US)

(72) Inventors: Thomas M. Meek, Sherman Oaks, CA (US); Brent Thorne, San Francisco, CA (US); Hasan Yasar, Baden, PA (US)

(73) Assignee: Intelidigital Corp., Valencia, CA (US)

( * ) Notice: Subject to any disclaimer, the term of this patent is extended or adjusted under 35 U.S.C. 154(b) by 0 days.

(21) Appl. No.: 15/607,597

(22) Filed: May 29, 2017

(65) Prior Publication Data

US 2017/0259117 A1 Sep. 14, 2017

Related U.S. Application Data

(62) Division of application No. 14/892,496, filed as application No. PCT/US2014/042330 on Jun. 13, 2014, now Pat. No. 9,662,538.

(60) Provisional application No. 61/834,836, filed on Jun. 13, 2013.

(51) Int. Cl.
| | |
|---|---|
| A63B 24/00 | (2006.01) |
| A61B 5/00 | (2006.01) |
| A61B 5/024 | (2006.01) |
| A61B 5/0488 | (2006.01) |
| A61B 5/08 | (2006.01) |
| A61B 5/113 | (2006.01) |

(52) U.S. Cl.
CPC ........ *A63B 24/0062* (2013.01); *A61B 5/0004* (2013.01); *A61B 5/02416* (2013.01); *A61B 5/0488* (2013.01); *A61B 5/0816* (2013.01); *A61B 5/1135* (2013.01); *A63B 2024/0065* (2013.01)

(58) Field of Classification Search
None
See application file for complete search history.

(56) References Cited

U.S. PATENT DOCUMENTS

| | | | |
|---|---|---|---|
| 4,355,645 | A | 10/1982 | Mitani |
| 5,316,009 | A | 5/1994 | Yamada |
| 5,358,519 | A | 10/1994 | Grandjean |
| 5,924,984 | A | 7/1999 | Rao |
| 6,361,494 | B1 | 3/2002 | Lindenthaler |
| 6,507,944 | B1 | 7/2003 | Hadas |
| 6,736,759 | B1 | 5/2004 | Stubbs |

(Continued)

FOREIGN PATENT DOCUMENTS

JP 2011-025038 2/2011

*Primary Examiner* — James B Hull
(74) *Attorney, Agent, or Firm* — Ferguson Case Orr Paterson

(57) ABSTRACT

A fitness system for enhancing the effectiveness and efficiency of physical training and/or exercise by a user comprises uses (1) a plurality of sensors that are worn by an exercising user and which generate data concerning monitored body processes pertaining to the exercise's effects on the user's body, (2) a processor operates under software control for processing, storing, and analyzing the data, and sending the processed data to a host device using a wireless communication protocol to communicate desired adjustments to the exercise in real time. The host device can be a smartphone, tablet computer or other web accessible device that can display and communicate bilaterally with the processor.

10 Claims, 12 Drawing Sheets

(56) References Cited

U.S. PATENT DOCUMENTS

| | | |
|---|---|---|
| 2008/0220941 A1 | 9/2008 | Shaw |
| 2009/0240193 A1 | 9/2009 | Mensinger |
| 2010/0120585 A1 | 5/2010 | Quy |
| 2010/0256914 A1* | 10/2010 | Hutin ............... E21B 41/00 702/9 |
| 2011/0269601 A1 | 11/2011 | Nelson |
| 2012/0041279 A1* | 2/2012 | Freeman ............ A61B 5/0205 600/301 |
| 2014/0031703 A1* | 1/2014 | Rayner ............ A61B 5/02055 600/484 |

* cited by examiner

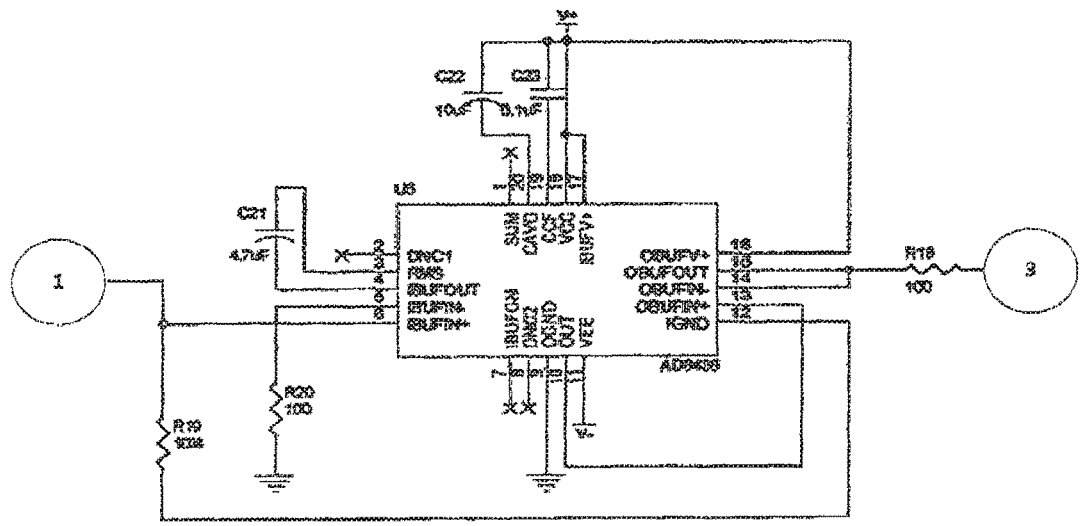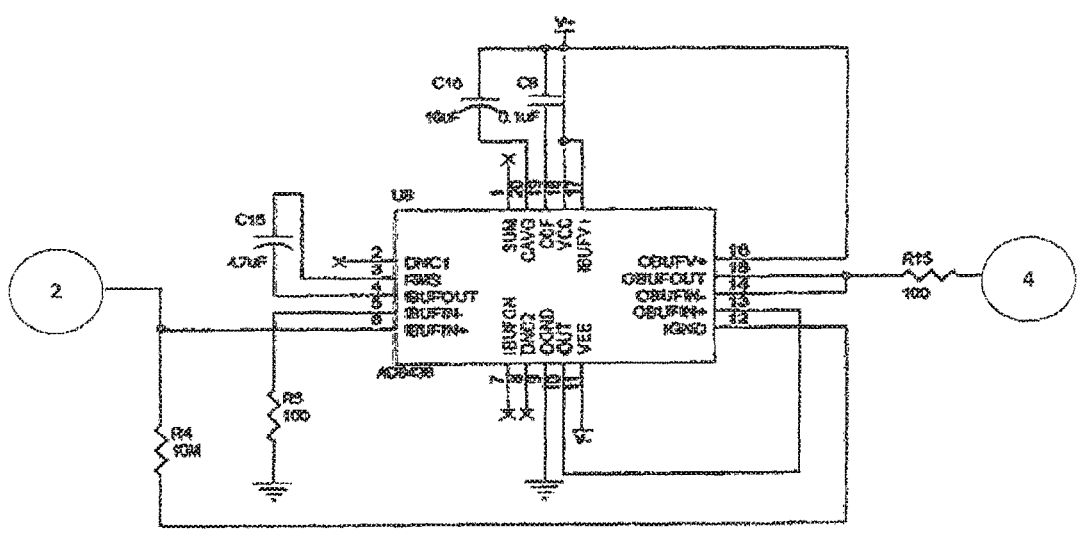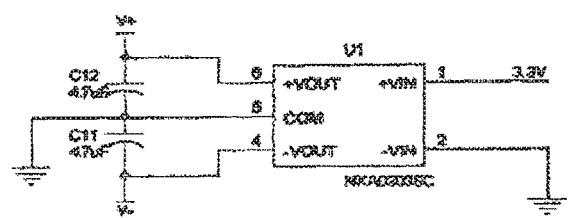
Fig. 3B

ACME HEALTHCARE, LLC
WELCOME TO MUSCLE MONITORING PORTAL.
PLEASE ENTER THE PATIENT'S INFORMATION BELOW TO GET STARTED

FIRST NAME
[ Enter patent's first name ]

LAST NAME
[ Enter patent's last name ]

ADDRESS
[ Enter patent's address ]

HOME PHONE
[ Enter patent's home phone number ]

CELL PHONE
[ Enter patent's cell phone number ]

EMAIL ADDRESS
[ Enter patent's email address ]

AGE
[ 28 ]

WEIGHT
[ 90.7185 KG ]

HIGHT
[ 1.8796 M ]

HEART RATE
[ 78 BPM ]

BLOOD PRESURE
[ 76/120 ]

Fig. 10

SYSTEM FOR OPTIMAL PHYSICAL EXERCISE AND TRAINING

This is a divisional application of U.S. application Ser. No. 14/892,496 filed Nov. 19, 2015, now U.S. Pat. No. 9,662,538 issued May 30, 2017, which is a national phase application of PCT/US2014/042330 filed Jun. 13, 2014, which claims benefit of Provisional Application No. 61/834,836 filed Jun. 13, 2013, each of which are incorporated by reference as if set forth fully herein.

FIELD OF THE INVENTION

This invention pertains to exercise and fitness systems.

Although there are numerous types of exercise machines and devices available for building strength and/or endurance, there is a need for a system that assists a user in ensuring that the exercise regimen being employed is efficient and effective. For example, there are optimum zones within one should maintain a breathing rate, heartbeat, etc. There also comes a point wherein muscles receive insufficient oxygen, so that further exercise or repetitions of an exercise movement are of little or no benefit and, in fact, could cause injury. Moreover, these zones and points vary from person to person, and also vary during the course of training.

SUMMARY OF THE INVENTION

The fitness system for enhancing the effectiveness and efficiency of physical training and/or exercise by a user uses (1) a plurality of sensors that are worn by an exercising user and which generate data concerning monitored body processes pertaining to the exercise's effects on the user's body, (2) a Muscle Exercise Monitoring System (sometimes hereinafter referred to as the "MEMS") device for processing, storing, and sending data, (3) a host device(s) in digital communication with the processor via a wireless communication protocol for receiving the processed data and (4) a display device that is preferably a component of the host device(s) or one or more client interfaces on any web accessible devices, for display and/or control in a visually comprehensible format to the user and/or a trainer.

If desired, means can be provided for establishing a data communication link between the processor and a cloud-hosted service that provides for data aggregation service.

The MEMS herein comprises a processor operating under software control to record and evaluate the incoming sensor data in order to define, update and communicate desired adjustments to the exercise in real time for optimal training and exercise. Incoming sensor data, for example, may include pulse rate, breathing rate and capacity, blood and breath chemistry, and the exercise activity rate and number of repetitions in contractions of one or more monitored muscles. Visual or audible feedback to the user (or the user's trainer) provided by the host device may, for example, advise the user to increase or decrease the rate of muscle contraction/release, adjust the rate or volume of breath upward or downward, etc. Consequently, the system herein provides the trainee, trainer or technician with objective feedback in order to obtain optimal results from the training/exercise session.

The sensors may, in whole or in part be formed on Spandex® (or other suitable material) that is placed over a muscle group, skeletal joint, or around the chest cavity, head, wrists or ankles, or feet.

Accordingly, exercise-related data is collected in real time and stored locally within the processor, a nearby computer, a wearable data storage device, and/or other data storage device in direct or indirect electronic communication with the sensors. A standard wireless data communication protocol such as Bluetooth®, IEEE 802.11a/b/g/n, or other suitable protocol can be conveniently used to display exercise-related data and information in real time on the user's smartphone or other display device. Where a cloud service is utilized, locally stored data can be uploaded to the cloud when connectivity is established. Cloud sessions can be utilized to permit users to share and/or compare exercise sessions.

Preferably, the processor collecting data from sensors attached to the user's body is a small wearable device having the dimensions and weight that permit it to be worn comfortably and barely noticed by the user, if at all. The processor responds to the incoming data streams from the sensors in accordance with target parameters manually imputed or pre-programmed into the host device, whereby the information and/or data fed back to the user can represent real-time performance parameters, the difference between actual and optimal parameter values, and/or the direction or degree to which the exercise movement should be adjusted. The host device may be any web client compatible device such as a smart phone, tablet computer, "wrist-watch" computer or other electronic device that can provide a display for viewing by the user. The term "host device" will hereinafter be used to conveniently refer to any or all of the foregoing.

Sensors

The processor provides a number of data ports to which the sensors are electronically coupled for data communication. Electronic coupling can be via hard wire, wireless protocol or a combination thereof.

Among the sensors that can be utilized are sensors that measure (1) bioelectrical signals from monitored muscles or muscle group(s), (2) heart rate, (3) blood translucence indicative of the 02 content of the blood, (3) muscle flexure, (4) air flow into and/or out of the user's lungs, (5) pressure under the soles of the feet and (6) physical position of the user's body (i.e., data responsive to the position of video references placed on the user' s body for providing photometric data via computer vision). Other sensors may be utilized as well and are within the scope of the invention.

The bioelectric sensors preferably comprise electrodes attached to the muscle group in such a way as to collect surface electromyography ("sEMG") signals that measure the amount of electrical activity released by muscles as they contract, due to biochemical ion movement during muscle activation and recovery. The preferred muscle sensor does not penetrate the skin to collect the signal. As a muscle becomes fatigued the changes to the bioelectrical signal are measured using spectral analysis and displayed as frequency power density. The muscle's electrical signal frequency-power spectrum changes as the monitored muscles use adenosine triphosphate ("ADT") during the exercise and produce waste products such as $CO_2$ and lactic acid.

In accordance with the invention, these signals are processed by the system herein to detect proper technique and muscle fatigue.

Pulse rate oximeters are sensors that measure both pulse rate and oxygen-related blood translucence. Blood oxygen becomes depleted at the point of physical exertion, and the detection of depletion produces a processed data signal that instructs the user to stop the exercise. When a muscle is overworked, there is little or no O2 in the muscle, so there is no benefit from additional reps, and an overworked muscle is also prone to injury. Heart rate data is used to enable the user to maintain an exercise level consistent with a target rate that optimizes the burning of fat rather than muscle as an energy source.

Air flow into and out of the user's lungs is derived from changing in the lung volume as preferably measured by a flexor-type sensor across the chest as to avoid the discomfort and disruption to the user of partially blocking the user's mouth or nose. Data from the flexor sensor is used in accordance with the invention to determine breath rate, and to thereby provide feedback to the user regarding breathing rate and volume and breathe control.

An accelerometer may be used in accordance with the invention to collect kinematic data about body movement and processes to count repetitions during repetitive exercise movements and for body-positioning information.

An array of pressure sensors attached to a body or placed in static exercise-mat may be used in accordance with the invention to collect balance point, pressure under body position, and body position. All sensors can be read at configurable frequency rates on different phases. The sensors interface with one or more main amplifier units that are part of the MEMS.

Video data can be generated and processed in accordance with the invention to provide photometric data.

Processor

The processor, operating under software control, reads and analyses the incoming signals from the sensors. Background noise is calibrated and filtered. The sensor data is transformed, analysed, compressed, packetized and time-stamped, and saved, and transmitted in a format compatible with a chosen wireless communication protocol, preferably Bluetooth®, for display and/or control.

The processor is preferably configured to engage in two-way communication with the host device so that target parameters can be communicated manually or under software control to the processor by the host device. Configuration of the processing unit is pushed by any PC at the initial setup via USB or ad-hoc WiFi connectivity. Future updates and configuration of the unit can be done through admin module of the web client interface. The target parameters are used by the processor in conjunction with real-time sensor data during the exercise/training session to transmit data for audible or visual presentation to the user pertaining to desired adjustments to the exercise routine for optimal results. Software and algorithms within the processor can be utilized to confirm that the muscle sensor is properly placed, since the signal pattern from the monitored muscle is predictable.

Host

The host device is preferably a smartphone, tablet computer or "wrist-watch" computer, but can also be any other electronic device that can provide a display that is viewable by the user, and preferably host processing software. Ideally, the smaller devices are preferred because the user can easily carry it on their body when running or moving around.

The host device preferably receives data from the processor via wireless communication, and preferably via a commonly available communications protocol such as Bluetooth®, displaying the data in a form that provides visual or audio feedback to the user as to how the then-current exercise movement pertains to their body's ideal workout and/or what changes the user should make to the movement at the moment. Signal data is processed under software control within the processor device, utilizing a wavelet analysis algorithm to transform from time domain to frequency domain, remove redundancy, compress and scale signals. The muscle group or other body process to be monitored can be menu-selected on the host device so that the incoming sensor signals may be filtered and processed for optimum signal-to-noise ratios and optimal display speeds.

The algorithm utilizes data from each repetition of the monitored exercise movement (i.e., the contraction and release of the monitored muscle or muscle group) including the duration and intensity of the contractions and releases. The collected reps for the exercise are conveniently hereinafter referred to as a "session". The data pertaining to each repetition of the session is preferably stored in a separate record, with the collection of records representing the session's data.

The duration and intensity of each monitored rep is compared by the processor to a desired duration and intensity, and transmitter to the host device to provide visual and/or audible feedback to the user is generated to speed up or slow down the movement or adjust the resistance to the movement to obtain optimum results.

The hosted application is preferably capable of searching for, and communicating with, one or more nearby fitness computers (processor device) so that the host can send commands or other data to selected computers and receive streamed data signals from each such fitness computer in a manner that relates incoming data to the computer that generated it. The processor device processes the signal data to create a real-time model of the user's exercise variables that enable the user to tailor the exercise for optimum results by comparing exercise signature signals. Accordingly, visual and/or audible cues can be generated back to the user in real time as data is acquired, processed and analysed.

One host device can monitor multiple processors, or one trainee can be monitored by multiple host devices, depending on how the system is configured. The processed data can indicate when the monitored muscle is fatigued to the point where the exercise flexure/extension should stop, whether the breath rate and pulse rate signatures are correct, whether the muscle is being used correctly, whether the heart rate is proper for the breath rate, the number of reps experienced, whether the user is inhaling and using O2 properly, whether the muscle is using O2 efficiently, etc. All of this can be combined to determine if the user is exercising correctly and optimally. The display can show the user that the proper muscle(s) arc being worked, when the monitored muscle group is properly exhausted, and whether the exercise movement should be sped up or slowed down to match the ideal waveform for that movement.

These and further details of the invention will be apparent to those of ordinary skill in the art from reading a description of the preferred embodiment of the invention described below, and of which the drawing forms a part.

DESCRIPTION OF THE DRAWINGS

FIGS. 3A-3C are partial figures of a circuit diagram of the preferred processor 50 illustrated in block diagram form in FIG. 1, while FIG. 3D shows the whole formed by the partial figures and indicates the positions of the parts;

FIG. 10 is an illustration of a preferred Web interface landing page; and

CURRENTLY PREFERRED EMBODIMENT

Preferred MEMS System Components

Figure 1:
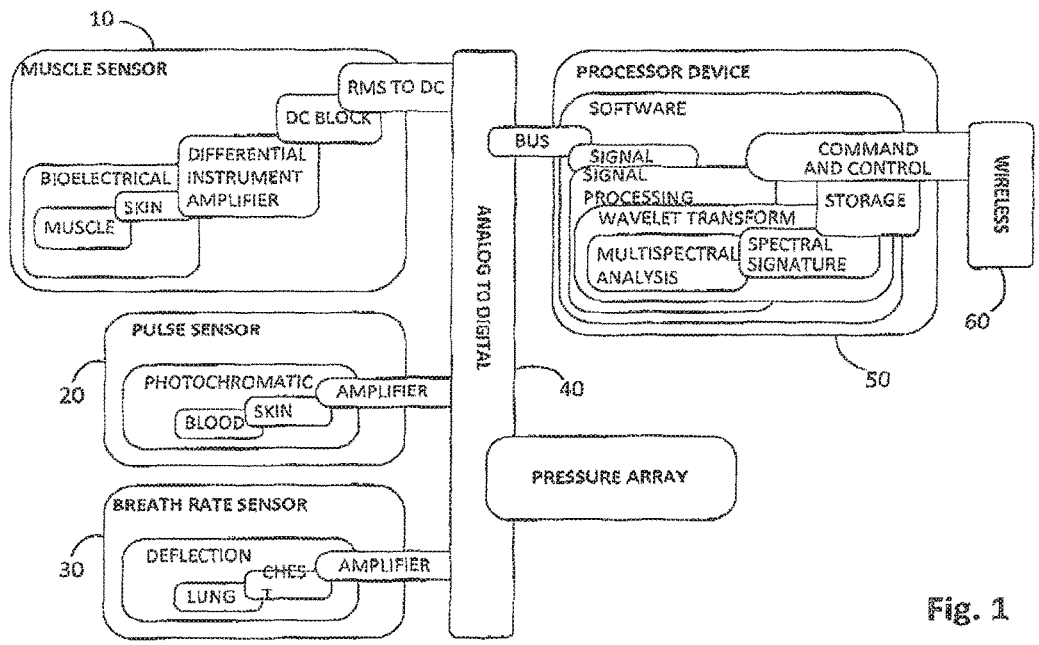
FIG. 1 is a block diagram illustrating a preferred system, constructed in accordance with invention.

FIG. 1 is a block diagram illustrating a preferred system constructed in accordance with invention wherein a muscle sensor 10, a pulse sensor 20 and a breath rate sensor 30 are electrically coupled for communication with an analog-to-digital converter 40.

A muscle signal amplifier associated with the muscle sensor 10 preferably has a very high input impedance of approximately 10 terra-ohms, and receives an electrical signal from the monitored muscle through the user's skin. The preferred muscle sensor comprises three electrodes, one of which is positioned over a suitable location such as the user's elbow, to act as a signal reference point. The remaining two electrodes are preferably places at the end of the muscle and the middle of the muscle, respectively. Alternatively, it may be desirable to place the two remaining electrodes on alternate sides of a monitored muscle.

The sensors may include electrodes that are formed on Spandex® (or other suitable material) that is placed over a muscle group, skeletal joint, or around the chest cavity, head, wrists or ankles, or feet.

The preferred pulse sensor 20 is a Pulse Sensor Amped™ offered at www.pulsesensor.com. It includes a photochromatic blood oxygen sensor that measures the color of the user's blood through the skin, and may conveniently be attached at the ear lobe or fingertip.

Figure 4:
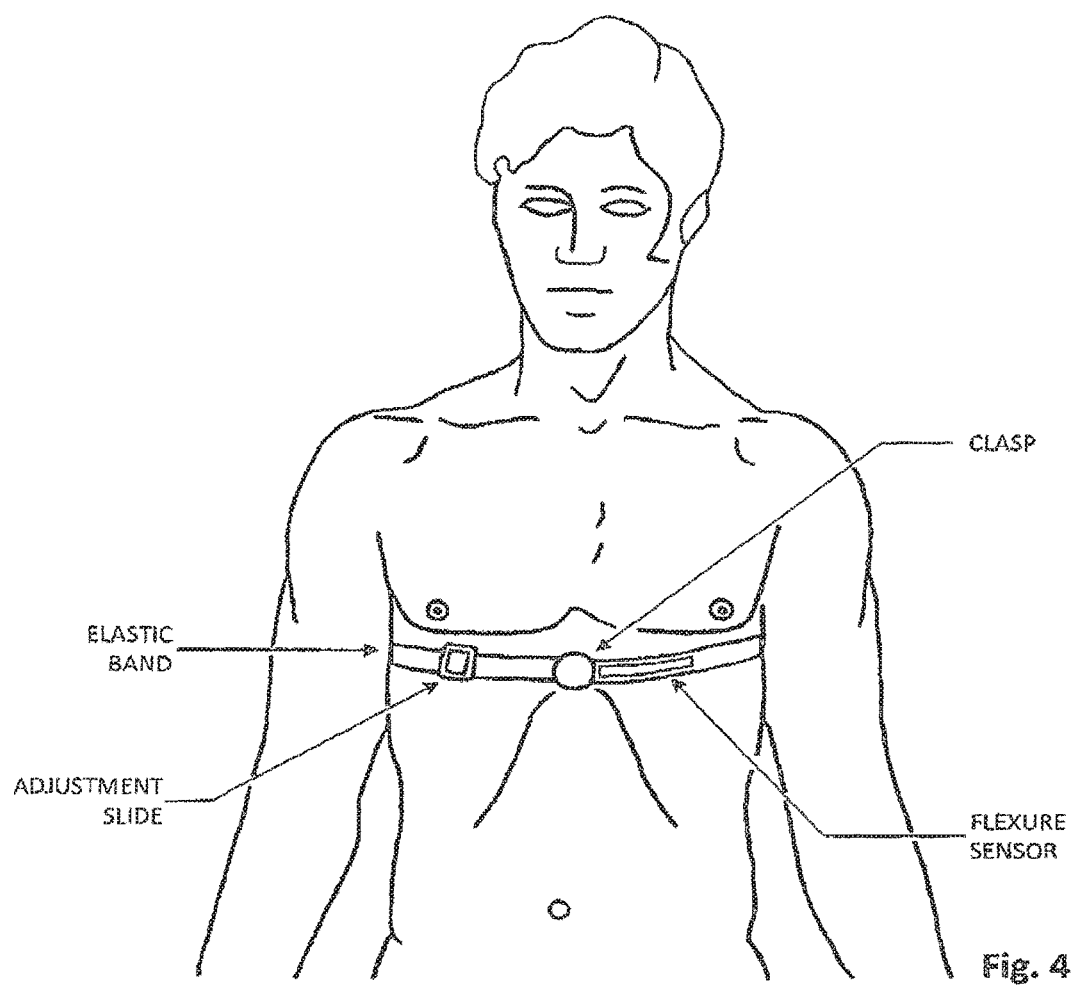
FIG. 4 illustrates a user wearing the preferred breath rate sensor.

The preferred breath rate sensor (also illustrated in FIG. 4) is of the chest strap variety and measures chest deflection and deflection rate; the chest strap is preferred because it is more comfortable and less distracting than other type of sensors such as those in mask for that fit over the nose or mouth.

Other sensors may be utilized as well, but the foregoing are illustrated and described for illustrative purposes, and it should be understood that the invention is not limited to utilization of the foregoing sensors.

The sensors generate signals in response to the monitored body parameter. The muscle sensors, for example, generate a train of pulses as ions move as the result of biochemical reactions during muscle contractions and releases during repetitive exercise movement. The remaining sensors produce analog signals as well, which may be generally sinusoidal (as the breath rate sensor), spiked (as the pulse rate monitor) or relatively ramped (as the O2 monitor).

The signal from each sensor is digitized by the analog-to-digital converter 40, and the resulting signal values are fed over a bus to the CPU of a processor 50 which processes, compresses, packetizes, and time stamps the sensor signal values, and then transmits the packets wirelessly to a host device via a Bluetooth® communicator so that the user's host device, and/or that of a desired third party, can be utilized to store and/or display the sensor data in a format easily assimilated by the user, either visually and/or audibly as hereinafter described. The currently preferred processing algorithm is from an open-source library called the WAILI wavelet transform library.

Each of the preferred sensors can include all the components illustrated in FIG. 1, including its own A/D converter and Bluetooth® transmitter; alternatively, the sensors can be multiplexed to time-share the A/D converter and Bluetooth® transmitter. Other wireless communication standards can be used that are compatible with the chosen host device(s) without departing from the scope of the invention.

Figure 2:
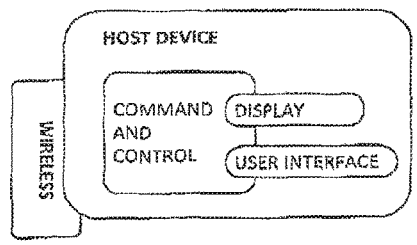
FIG. 2 is a block diagram of a preferred host device used in accordance with the invention.

FIG. 2 is a block diagram of a preferred host device used in accordance with the invention, and is shown to include means for de-packetizing the incoming wirelessly transmitted data, decompressing the resulting data if necessary, storing it at least temporarily and displaying it in a readily understandable format to a viewer that is most likely the user. Compressing and packetizing the data permits a maximum amount of data to be transmitted within the restricted amount of wireless transmission bandwidth available. Data is preferably recovered using statistical wavelet analysis; decompression may accordingly not be necessary if the wirelessly transmitted data represents, at least in part, sensor signals that have been converted from time-domain values to frequency-domain values as part of the signal processing done within the processor device of FIG. 1 to thereby inherently reduce the amount of data needed to be transmitted to a level meeting any limitations of available bandwidth. The preferred host device can communicate bilaterally with the processor to enable the user to input desired exercise or body function parameters, set targets, etc.

Figure 3A:
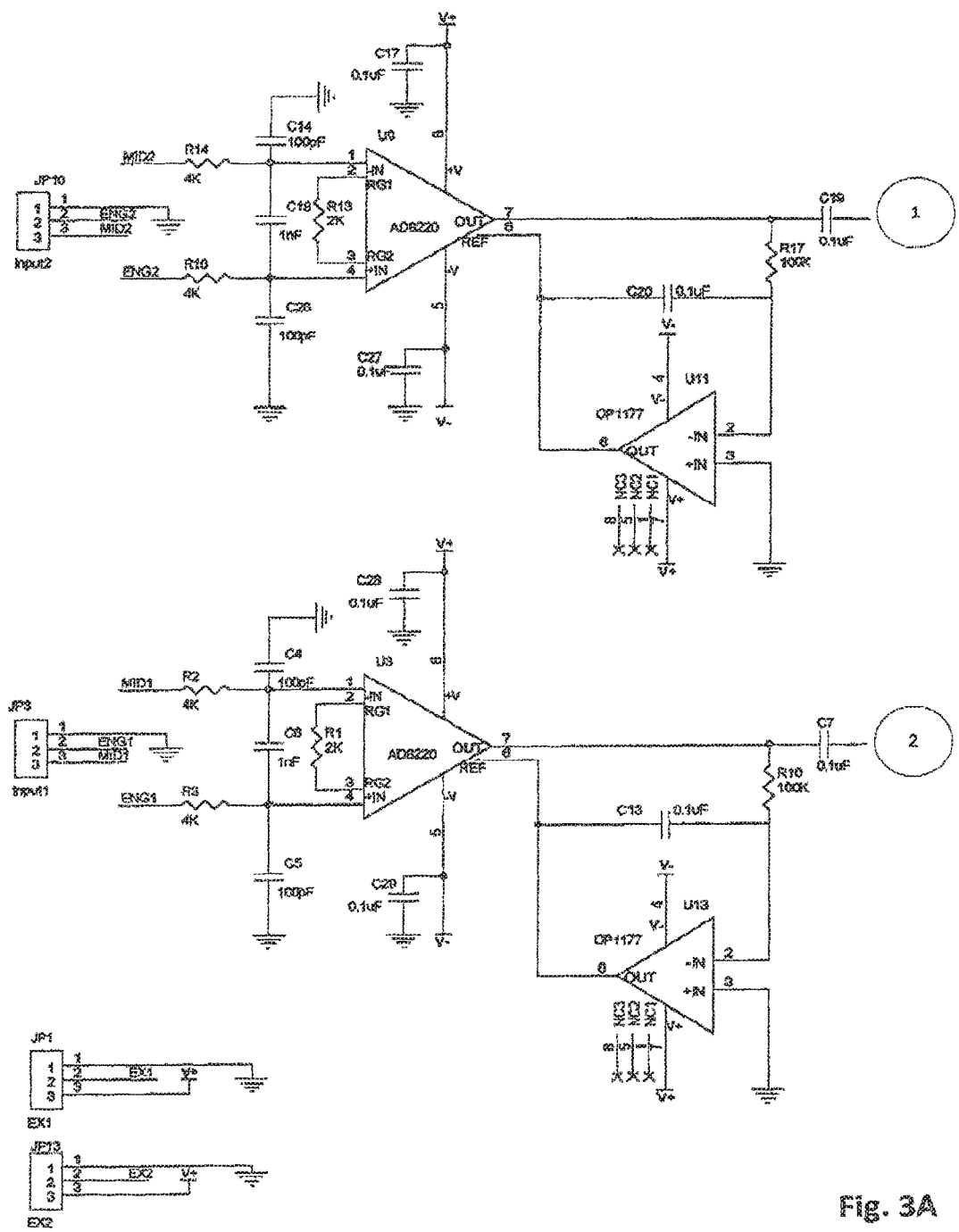
Figure 3C:
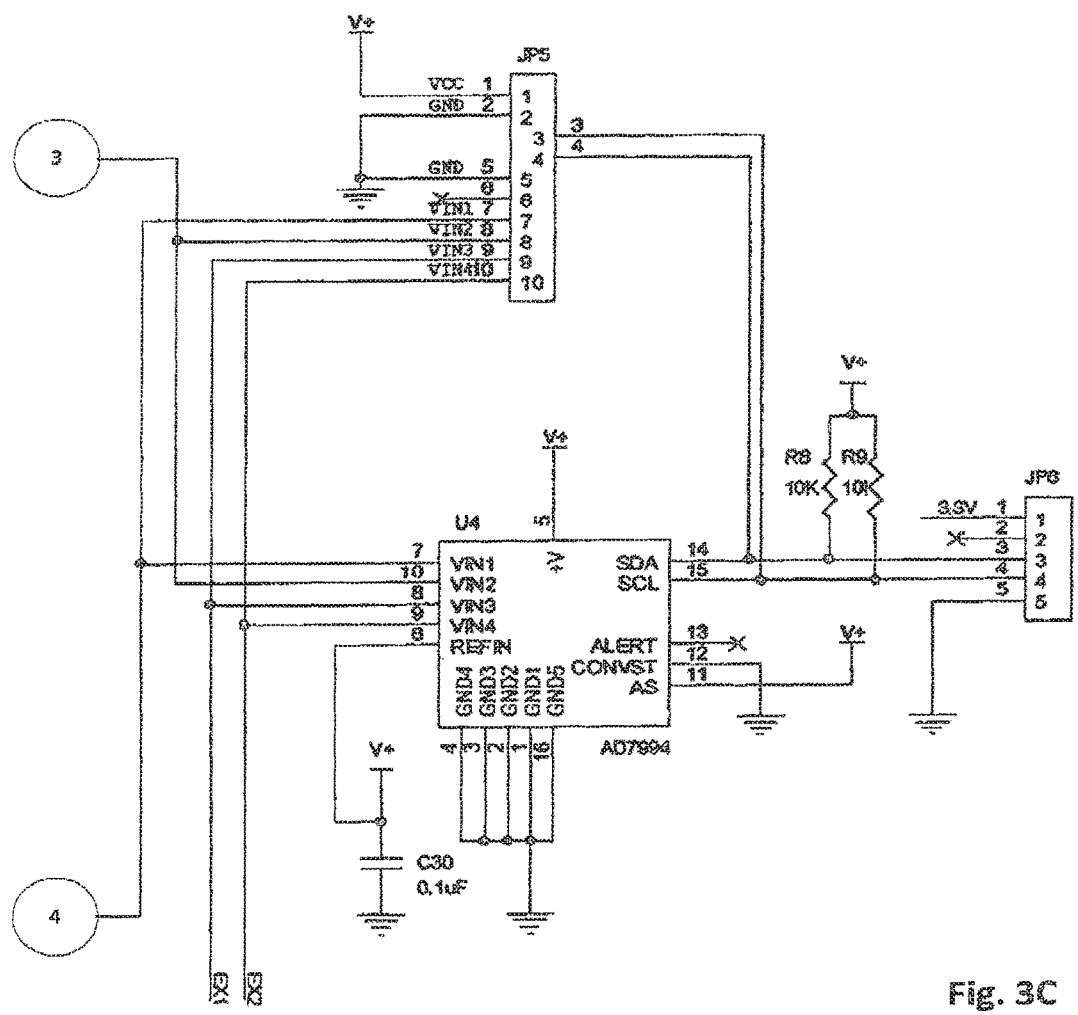
Figures 3A, 3B, 3C, 3D:
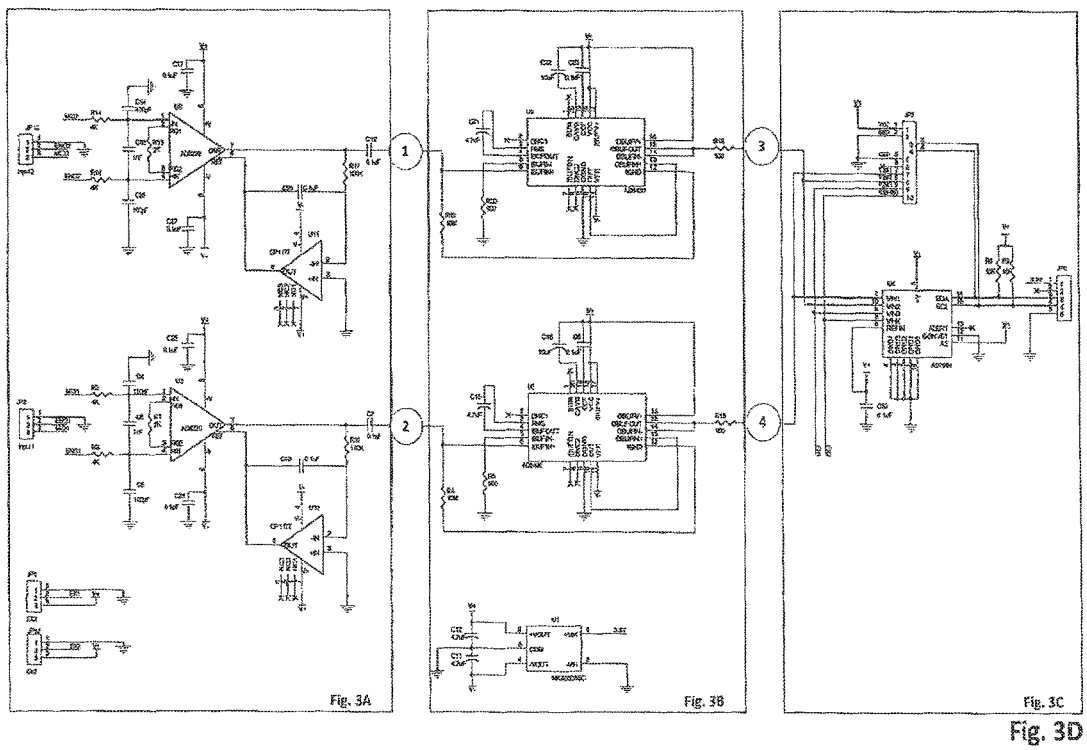

FIGS. 3A-3C illustrate a circuit diagram of the preferred processor 50 illustrated in block diagram form in FIG. 1. The processor includes a pair of input jacks JP3, JP10 to which a pair of muscle-monitoring sensors can be respectively electrically coupled. Two additional, jacks JP1, JP13 are provided for electrically coupling the pulse sensor and breathe rate sensor to the processor.

There are three electrodes associated with each of the preferred muscle sensors, and each of the jacks JP3, JP10 accordingly have three connection points. Two of the electrodes of a muscle sensor are preferably positioned to monitor the left and right sides of the monitored muscle or muscle group or, alternatively, complementary muscles such as the user's bicep and tricep, with the two consequential signals being respectively coupled to pins 2 and 3 of the jack. The third electrode is preferably positioned at a signal reference point on the user's body and coupled via pin 1 to a circuit "ground" reference point; the user's elbow is a good reference location since there is virtually no muscle activity at that point that adversely affects signal detection and processing.

The two signals from each sensor are respectively coupled by the jacks to input pins 1 and 4 of a differential amplifier, preferably an Analog Devices AD8220. Thus, jack JP10 couples the applied sensor signals at pins 2 and 3 to the input pins 4 and 1 of amplifier U9 as illustrated, and JP3 does so to amplifier U3. An active low-pass filter comprising amplifier U11 (preferably an Analog Devices OP117) is electrically coupled between the output of amplifier U9 and the "reference" pin 6 of that amplifier as illustrated. U11 is a differential amp and minimizes environmental EMI.

Similarly, an active low-pass filter comprising amplifier U13 is electrically coupled between the output of amplifier U3 and its "reference" pin 6 as illustrated. Active filters are preferred because they provide a sharp cut-off frequency. Active filter amplifier U13 provides negative feedback in effect to reduce the gain of amplifier U3 and thereby avoid amplification of high frequency noise. U8 as configured, functions as a DC block and an RMS block and increases the input impedance. DC block rejects EMI that can cause DC drift so to get pure AC at output to the processor device.

The analog signals indicative of the real-time muscle sensor signals at jack JP10 and JP3 are a train of pulses in nature, and are respectively outputted from pin 7 of amplifiers U9 and U3 to the non-inverting input pin 6 of respective RMS-to-DC converters US5 and U8 (preferably Analog Devices AD8436 units). DC level signals representing the RMS values of the respective sensor signals are outputted from pin 15 of the respective converters, and respectively applied as first and second inputs to pins 10 and 7 of a four channel analog-to-digital converter U4 (preferably an Analog Devices AD7994 configured as illustrated).

The remaining two input channels of the analog-to-digital converter U4 are electrically coupled to pin 2 of input jacks JP1 and JP13, respectively, to receive signals from the pulse sensor and breathe sensor. The signals from these sensors are modulated DC in nature.

In accordance with the preferred embodiment of the invention, all sensor signals are thereby sampled in a multiplexed manner by converter U4 and converted to digital data that is outputted in a multiplexed manner at pin 14 of converter U4 for subsequent transmission to the host device for display. Synchronous circuits are used to and sample the sensor signals at precise moments in time on a cycle basis, channels 1 & 2 are on 10 khz, channels 3&4 are on 500 Hz. These analog signals are represented as a series of digital bits and the number of bits in the system defines the resolution of the conversion. With applying traditional sampling theory (i.e. Nyquist-Shannon theorem), a band limited sensors signal are represented with a quantifiable error by sampling the analog signal at a sampling rate at or above that sampling rate.

Prior to processing the digital values for wireless transmission, the digital data from the converter is read by the processor over I2C interface. The signal data is transformed from the time-amplitude domain into the time-frequency domain using a wavelet transformation. This transformation enables quick filtering and analysis of how the frequency response varies in time, decomposition of the spectral components and the comparison of spectral signatures.

With bidirectional communication possible, targets and algorithms can be updated from via Internet or cellular communications as, for example, by storing same on Flash ROM within the processor or host device.

Figure 5:
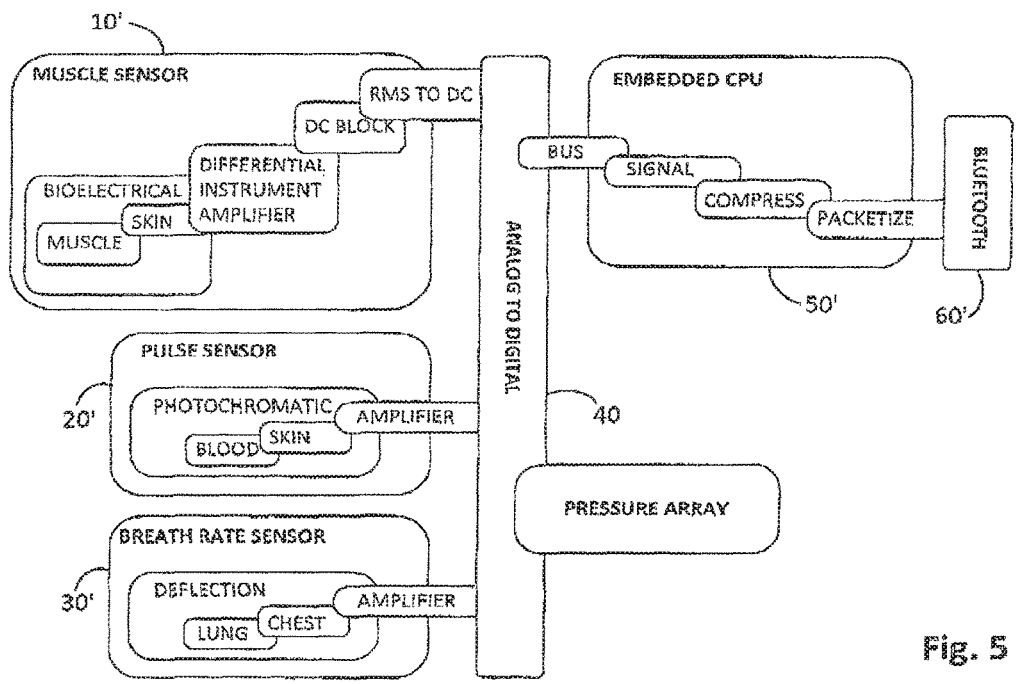
FIG. 5 illustrates an alternative embodiment of the invention.
Figure 6:
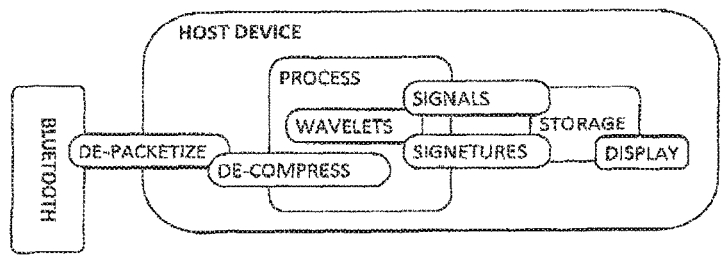
FIG. 6 illustrates an alternative embodiment of the host device.
Figure 7:
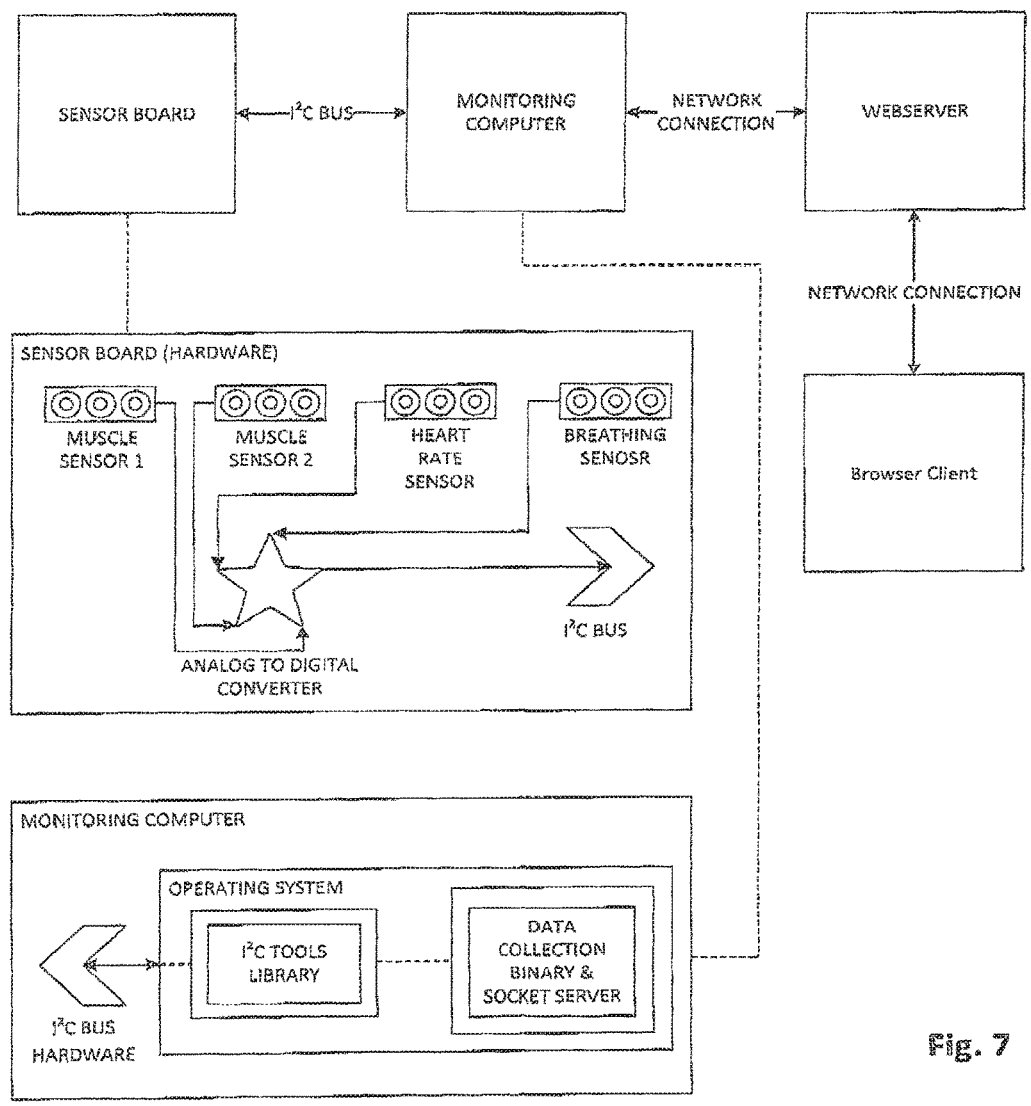
FIG. 7 is a block diagram illustrating the preferred MEMS system workflow.

FIGS. 5 and 6 illustrate an alternative embodiment of the invention. FIGS. 5 and 6 are analogous to FIGS. 1 and 2. In this embodiment, signal processing is done in the host device. Accordingly, sensor signals are digitized, compressed and packetized prior to wireless transmission. No conversion from time domain to frequency domain values is performed prior to wireless transmission, although one could do so if one wished. The digitized values are de-packetized, decompressed and analyzed within the host device, which then displays data for viewing by the user in light of parameter targets programmed into the host device. Preferred MEMS Software Components FIG. 7 illustrates overall software workflow. The operating system on the MEMS is a customized Raspbian distribution. The kernel remains largely unmodified but certain libraries such as i2c-tools have been installed and configured to allow access to and communication over the $i^2c$ bus. Firmware enables WiFi, Bluetooth, USB and Ethernet connectivity on the boot. The firmware communication modules are written in C code. The C code utilizes pthread and $i^2c$ libraries to read from the sensors and present the data to a client connected over a top socket.

Figure 8:
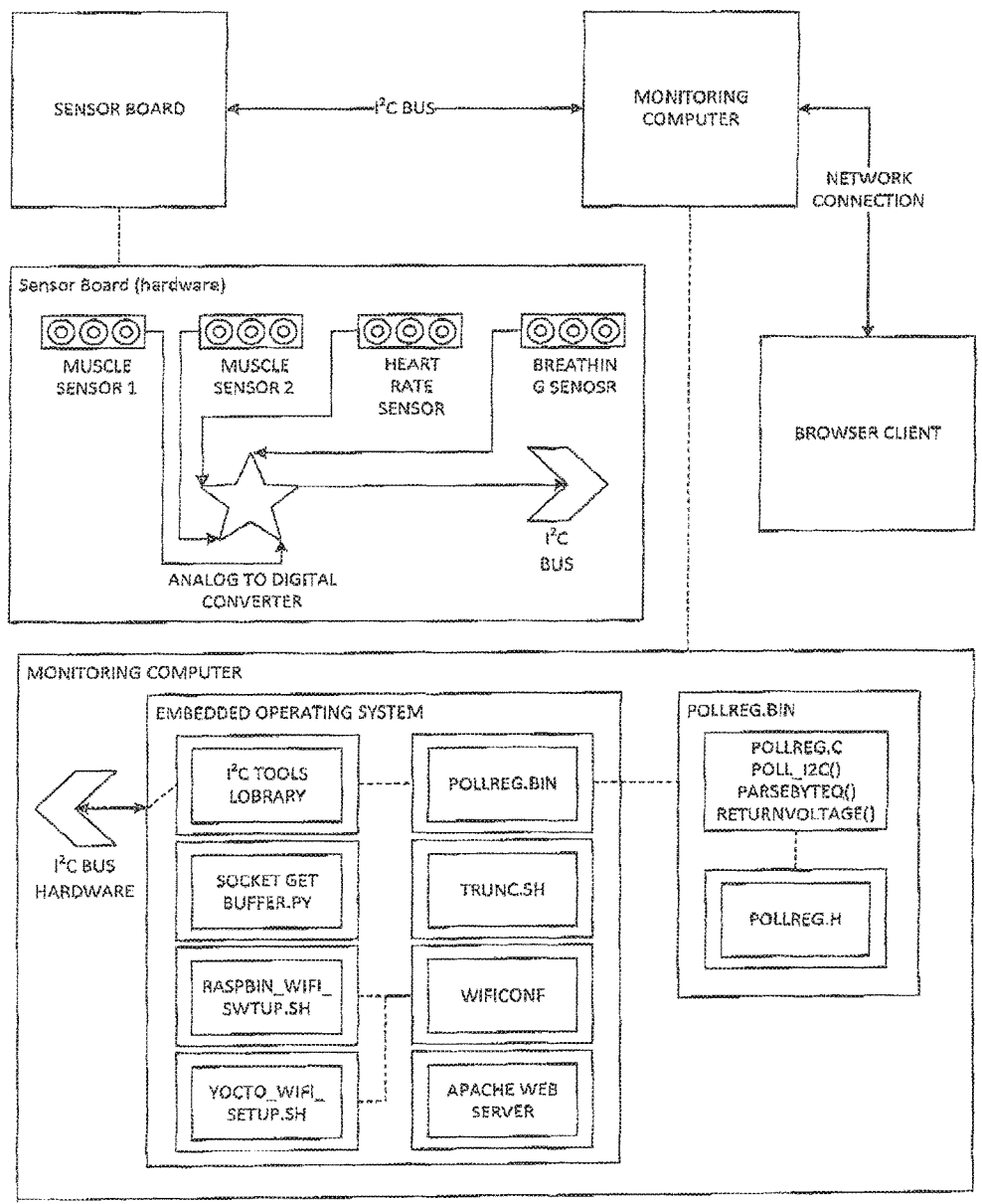
FIG. 8 is a block diagram illustrating the preferred MEMS firmware.

FIG. 8 is a block diagram of the data collection and socket server modules. I2C registry is configured to read multiple sensor data at 25 Microhertz. On each reading cycle, data is being parsed and identified type of sensor. Reading voltage value is calibrated and filtered to normalized value. There is a Python client script that runs as part of the web interface code that collects data from the C sensor poller and passes the data to the clients and user interfaces.

When the RaspberryPi device loads, all communication modules are configured on the boot. Raspbian_Wifi_Setup.sh loads the wifi.conf file from attached usb drive and configures the WiFi. Once the device boots, it loads a script to connect the device to a wireless network whose credentials are loaded at boot from a flash drive. The credentials are stored on the flash drive in the correct format by entering the correct information into a Java program running on the configuring user's computer. Then trunc.sh runs and clears the local disk storage freeing up space for a new session. Then pollreg.bin and asynchronously collects sensor data and serves that up through a tcp socket to browser client for display and analysis.

Sensor data will begin collection and broadcast in real time as soon as the device is powered on using the data communication and tcp socket module.

On every 25 microsecond, i2c bus read by data collection routine on multithread application. After parsing bus data, each channel has its own thread and handles memory array by using continues wavelet transforms theory. As a result, sensor data is converted into time-domain. Basically, each digital reading value has date/time stamps on a millisecond level. Graph engine modules read from the memory array and then draw the dots for each value/time and connect each point on continuous bases. For predicting the behaviour of muscle, heart and breath activities, time-series data is analyzed and classified based on Bayesian regression methods. Classified data is historically saved and run through machine learning engines where linear regression and spectral clustering are being used to generate next set of data for any given time-frame.

Figure 9:
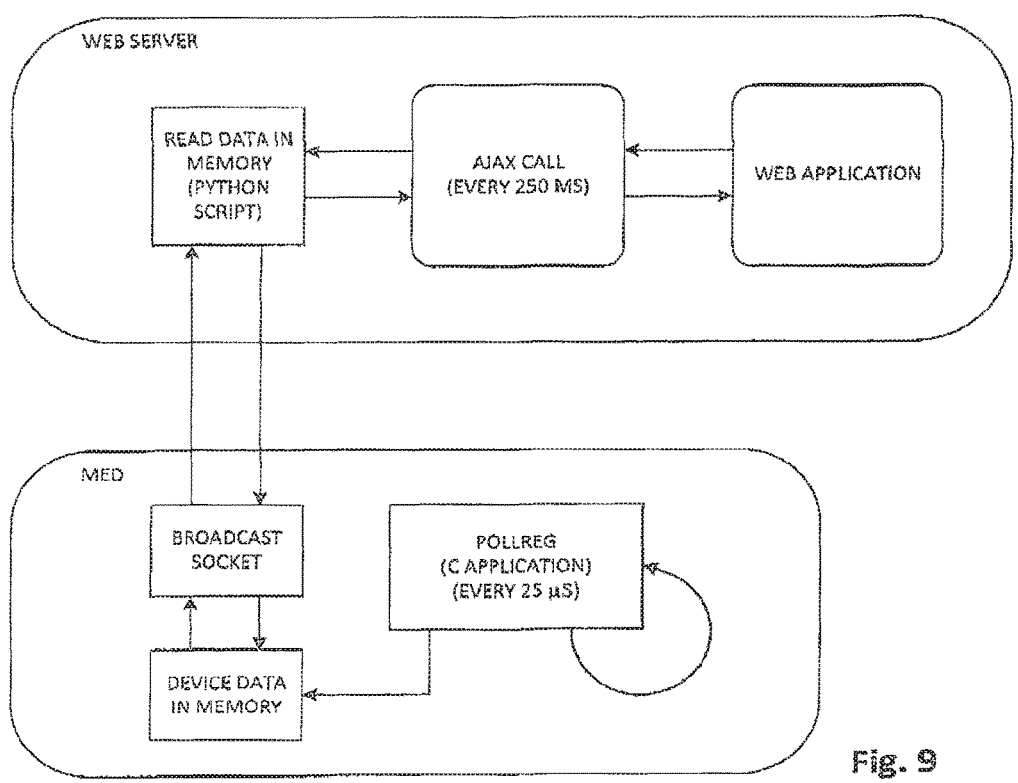
FIG. 9 is a block diagram illustrating Web interface workflow.

FIG. 9 is a workflow of the web application interface of the MEMS and how sensor data is being displayed on interface. On the MEMS, a C application polls the sensors every twenty-five microseconds. It stores the values from each sensor with a date and timestamp (i.e. [[channel1, channel2, channel3, channel4, datetime], . . . ]). The C application also opens a socket for communication with a web service. On the graphing page of the web application, an AJAX script is run every 250 microseconds. This script calls a python script that connects to the socket on the MED. It pulls all data stored in memory, and passes it back to the web application. The web application then parses the data and puts it the appropriate graph.

Signal data is read and processed as time series data. Fractal behaviour methods are used on display sensor data.

While monitoring muscle activities, the host can detect unique behaviour of target (muscle groups/exercise type etc). Wavelets methods and algorithm are used to detect specific behaviours.

All sensor data, Muscle, Breath, and Heart Rate sensors combined display/chart/archive overall Aerobic-endurance, Anaerobic power-endurance, sustained-power, and strength-power activities. The combined sensor data perceives ATP and CP depletion, lactic acid accumulation/fatigue effect, and calcium ion build up in the muscles at any given time, as well as, VO2 max data through oxygen consumption/depletion and blood pH decrease. This and basic data information, such as height, weight, age, sex, activity level, bmi, etc. produce an accurate analysis of the users overall ability, strength, and endurance at any given exercise. The user's calorie, fat burned, energy consumption/fuel, and recover times can be calculated. The data collected can be recorded and collected in physical activities natural environment via in practice, in game, the gym etc.

Using collected flex sensor data, MEMS determines the oxygen inhaled and exhaled by heart rate readings equal $O_2$ consumption and presents it to the user via web interface. Results for VO2 measurements are generally displayed in L/min (i.e. litres per minute, representing the volume of oxygen consumed by the user's entire body each minute) or, to account for differences in total body mass, in mL/kg/min (i e milliliters per kilogram per minute, representing the volume of oxygen consumed each minute per kilogram of body mass).

The method for measurement of VO2 can be summarized according to the following equation . . .

$$VO2=[VI \times \% \; O2VI]-[VE \times \% \; O2VE]$$

where VI=volume of inspired air;
 % O2VI =percent oxygen in inspired air (flexor sensor);
 VE=volume of expired air (flexor sensor); and
 % O2VE=percent oxygen in expired air Using Flexor and heart rate sensors together, MEMS monitors $O_2$ consumption and maximum exertion. Within the above equation, VO2 max equals maximum millilitres of oxygen consumed in a minute/body weight (in kilograms).

Using Flexor, muscle and heart rate sensors together, it is possible to determine ATP & CP depilation. $O_2$ intake and heart rate during muscular contraction from peak performance to fail equals ATP & CP depletion. Muscle recovery rate is calculated from monitored heart rate recovery and monitored breath consumption following cessation of exercise. MEMS also enable to monitor the strength of muscle on calculation peak performance. The following methods are used to calculate peak performance for different user profile.

For men: Calories Burned=[(Age×0.2017)+(Weight×0.09036)+(Heart Rate×0.6309)—55.0969]×Time/4.184.

For Women: Calories Burned=[(Age×0.074)—(Weight×0.05741)+(Heart Rate×0.4472)—20.4022]×Time/4.184.

Data Description

The application will be divided into a few primary data objects: Session, Person, and Company.

Figure 11:
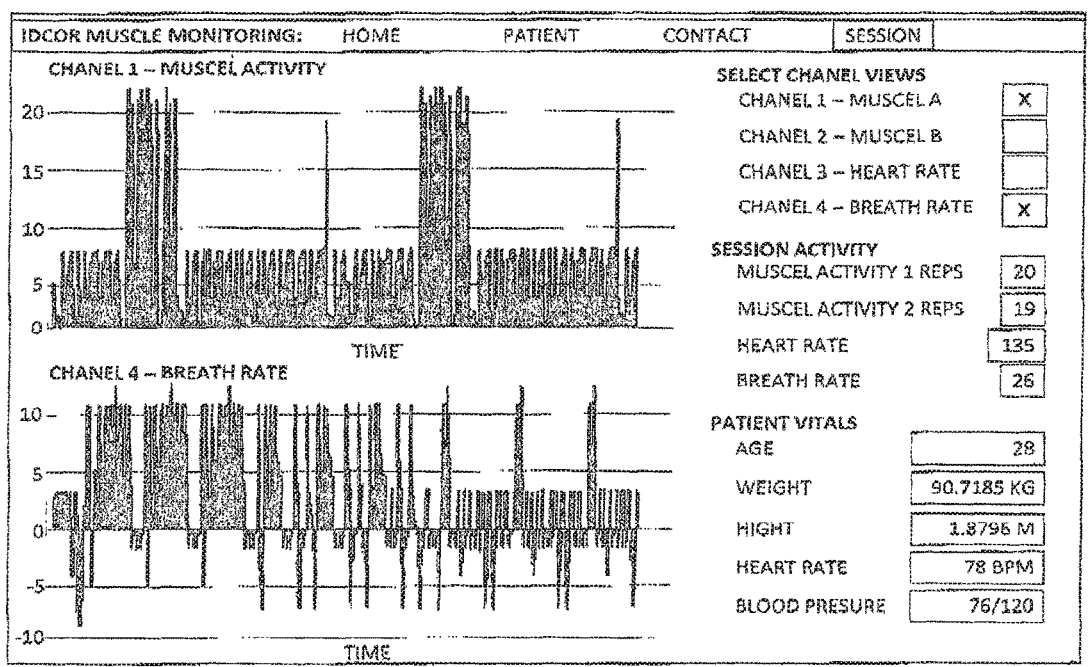
FIG. 11 is an illustration of representative data displayed on a host device or display device associated with the system herein.

Data Dictionary
Session Group
Session ID
Device ID
Company ID
Patient ID
Health Professional ID
Session Start Date/Time
MEMS identifier Sensor Data
 Time:Sensor Value
Session ID: A unique ID for each test session.
Device ID: A unique ID for MED used for particular session.
Company ID: Reference to the company operating the device.
Patient ID: Reference to the patient being tested.
Health Professional ID: Reference to the individual performing the test.
Session Start Date/Time: Timestamp of the start of the session.
MED Data: An array of key/value pairs for time to sensor value. (I.e. Data[[channel1, channel2, channel3, channel4, datetime], . . . ])
Person Group
Person ID
Company ID
Person Type ID
Name ID
Address ID
Mobile Phone
Home Phone
Work Phone
Email
Person ID: A unique ID for the person.
Company ID: Reference to the person's company (nullable).
Person Type ID: Reference to the type of person.
Name ID: Reference to the person's name.
Address ID: Reference to the person's address.
Mobile Phone: The mobile phone number.
Home Phone: The home phone number.
Work Phone: The work phone number.
Email: The person's email.
Company Group
Company ID
Company Name
Address ID
Office Phone
Office Email
Web Address
Company ID: A unique ID.
Company Name: The company's name.
Address ID: Reference to the company's address.
Office Phone: The mobile phone number.
Office Email: The person's email.
Web Address: The URL of the company's site.
User/Client Name
First Name
Last Name
Address
Line 1
Line 2
City
State
Zip
Person Type
Patient
Health Professional
Human Interface Design FIGS. 10 and 11 illustrate a web client interface mock-up. The landing page (FIG. 10) is a sample page where users are able to enter the basic information for a user. The form accepts the following data:
First name
Last name Address
Home Phone
Mobile Phone
Work Phone
Email Once all data is entered, the user clicks a "Begin Monitoring" button to tell the website to start collecting and plotting data on the graphs in the "Display Detail Page" (FIG. 11).

In one currently conceived configuration, for example, the user wears the sensors while exercising, and can view the sensed data in a graphic and/or tabular form on a smartphone or tablet computer that is in wireless communication with the processor to get real time feedback. The display can further provide visual and/or audio clues as to how the user can adjust the exercise movement for more efficient gain, such as by breathing more deeply, and more (or less) often, accelerating or slowing the pace of the movement, etc.

Although the present invention and its advantages have been described in detail, it should be understood that various changes, substitutions and alterations can be made herein without departing from the spirit and scope of the invention as will be defined by appended claims.

The invention claimed is:

1. A fitness system, comprising:
    a plurality of sensors which collect data related to at least one of a user's pulse rate, breathing rate, breathing capacity, blood chemistry, breath chemistry, exercise activity rate, and number of contractions of one or more monitored muscles of said user;
    a wearable device comprising a processor operating under software control, said processor comprising at least one differential amplifier, at least one converter, and a multiplexer,
    said processor in communication with said sensors and configured for receiving said data in real time from said plurality of sensors, processing said data into processed data, and sending said processed data to a host device, said processing said data by said processor comprising:
        receiving by the at least one differential amplifier at least some of said data and generating respective sensor signals and an RMS value associated with each of said sensor signals;
        converting by said at least one converter said RMS values to DC values;
        sampling by said multiplexer said DC values to produce a multiplexed digital signal representing the sampled values; and
        generating feedback information according to manually inputted or pre-programmed parameters in the host device and based on said multiplexed digital signals, wherein said feedback information represents real-time performance parameters, the difference between actual and optimal parameter values, and/or the direction or degree to which the exercise movement should be adjusted;
    a host device in communication with said processor and configured for receiving said feedback information; and
    a display device in communication with said host device and configured for displaying said feedback information.

2. The fitness system of claim 1, wherein said display device is integrated with said host device.

3. The fitness system of claim 1, wherein said processor is coupled via a data communication link to a cloud-hosted service for providing a data aggregation service.

4. The fitness system of claim 1, wherein said processor is configured to communicate with an external computer.

5. The fitness system of claim 1, wherein said processor is configured to communicate with a wearable data storage device via a wireless communication protocol.

6. The fitness system of claim 1, wherein said display device comprises a smartphone.

7. The fitness system of claim 1, wherein said host device comprises a web client compatible device.

8. The fitness system of claim 1, wherein said host device is selected from the group consisting of a smart phone, a tablet computer, and a wrist-watch computer.

9. The fitness system of claim 1, wherein said processor further comprises: local memory for locally storing data from said sensors; means for electronically communicating with a data-receiving cloud service; and means for uploading said locally stored data to said cloud service.

10. The fitness system of claim 1, said plurality of sensors comprising:
    at least one muscle sensor;
    a breath-rate sensor; and
    a pulse-rate sensor.

* * * * *